United States Patent
Schneider et al.

(10) Patent No.: US 7,169,923 B2
(45) Date of Patent: Jan. 30, 2007

(54) METHOD FOR PREPARING ALKOXYCARBONYLAMINO-TRIAZINES

(75) Inventors: Joerg Schneider, Weinheim (DE); Guenter Scherr, Ludwigshafen (DE); Hans Schupp, Worms (DE); Andreas Eichfelder, Maxdorf (DE); Alain Robert, Niederkirchen (DE); Martin Reif, Roemerberg (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/491,194

(22) PCT Filed: Oct. 23, 2002

(86) PCT No.: PCT/EP02/11837

§ 371 (c)(1),
(2), (4) Date: Mar. 31, 2004

(87) PCT Pub. No.: WO03/035628

PCT Pub. Date: May 1, 2003

(65) Prior Publication Data

US 2004/0249149 A1    Dec. 9, 2004

(30) Foreign Application Priority Data

Oct. 23, 2001 (DE) ............... 101 51 564
Apr. 25, 2002 (DE) ............... 102 18 617

(51) Int. Cl.
*C07D 251/70* (2006.01)
(52) U.S. Cl. ..................... 544/196; 544/200
(58) Field of Classification Search ........... 544/196, 544/200

See application file for complete search history.

(56) References Cited

U.S. PATENT DOCUMENTS 6,204,382 B1    3/2001    Flood et al.

FOREIGN PATENT DOCUMENTS

EP    0624577    11/1994
WO    0029829    5/2000

*Primary Examiner*—Venkataraman Balasubramanian
(74) *Attorney, Agent, or Firm*—Oblon, Spivak, McClelland, Maier & Neustadt, P.C.

(57) ABSTRACT

A process is described for preparing alkoxycarbonylamino-triazines by reacting di- or triaminotriazines with dimethyl carbonate in the presence of an alcohol and of an alkali metal or alkaline earth metal methoxide base.

8 Claims, No Drawings

METHOD FOR PREPARING ALKOXYCARBONYLAMINO-TRIAZINES

The present invention relates to a new process for preparing alkoxycarbonylaminotriazines by reacting di- or tri-aminotriazines with dimethyl carbonate in the presence of an alkanol and of an alkali metal methoxide or alkaline earth metal methoxide base.

EP-A-624 577 discloses preparing alkoxycarbonylaminotriazines by reacting triazines, such as melamine, with carbonic esters in the presence of a base. The melamine therein is generally reacted with a carbonic ester, e.g. dimethyl carbonate, in the presence of the parent alkanol of the carbonic ester, in this case methanol, for example, and in the presence of an alkali metal alkoxide, based on the parent alkanol of the carbonic ester, in this case methanol, for example, as said base. It goes onto describe reacting melamine, for example, with dimethyl carbonate in the presence of a higher alcohol, such as butanol or 2-ethylhexanol, and the corresponding sodium alkoxide, in this case sodium butoxide or sodium 2-ethylhexoxide, for example, as said base.

The procedure described therein is disadvantageous if the aim is prepare alkoxycarbonylaminotriazines other than methoxycarbonylaminotriazines or to prepare mixtures of differently substituted alkoxycarbonylaminotriazines. In such cases, indeed, it is necessary either to depart from dimethyl carbonate, a well-established reactant readily available on the industrial scale, and to conduct the reaction with higher dialkyl carbonates, which are generally expensive and more difficult to obtain on an industrial scale, or to use as said base alkoxides with higher alcohols rather than the likewise well-established and readily industrially available alkali metal methoxides, especially sodium methoxide, said higher alkoxides again generally being more expensive and more difficult to obtain than the methoxides.

Furthermore, the working up of the alkoxycarbonylaminotriazines from the reaction mixtures obtained, as described by EP-A-624 577, is not particularly advantageous. Generally speaking, the reaction mixtures are acidified or converted into an acidic solution. This is followed by extraction with an organic solvent. The organic extracts are then dried and freed from the solvent. Alternatively, following acidification, a solid is isolated by filtration and then washed and dried.

These methods are disadvantageous in the context of the industrial working up of reaction mixtures containing alkoxycarbonylaminotriazines, because they involve either the introduction of an extractant into the operation, or an expensive filtration technology. Moreover, in both cases, it is necessary to dry (remove water from) either the organic solution, by means of a drying agent, or the solid, under reduced pressure.

It is an object of the present invention to provide a new process for preparing alkoxycarbonylaminotriazines which no longer has the aforementioned disadvantages and which at the same time allow the preparation of a broad spectrum of mixtures of alkoxycarbonylaminotriazines which are isomeric and/or of mixed functionalization.

It is a further object of the present invention to provide a new workup method for reaction mixtures obtained in the preparation of alkoxycarbonylaminotriazines. Said method should avoid an expensive filtration technology and should not increase further the number of chemical components in the operation.

We have found that this object is achieved for the preparation of alkoxycarbonylaminotriazines of the formula I

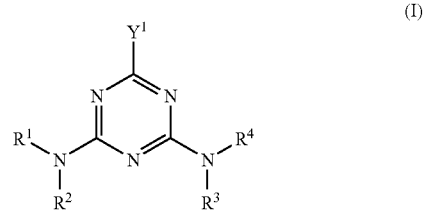

where
$Y^1$ is hydrogen, $C_1$–$C_4$-alkyl, phenyl unsubstituted or substituted by $C_1$–$C_4$-alkyl, $C_1$–$C_4$-alkoxy or halogen, or is a radical of the formula $NR^5R^6$, and
$R^1$, $R^2$, $R^3$, $R^4$, $R^5$ and $R^6$ independently of one another are each hydrogen or a radical of the formula COOX or X, where X is $C_1$–$C_{13}$-alkyl, whose carbon skeleton may be interrupted by 1 or 2 oxygen atoms in ether function, with the proviso that at least one of the radicals $R^1$ to $R^4$ or, if $Y^1$ is $NR^5R^6$, at least one of the radicals $R^1$ to $R^6$ is COOX, by reacting a triazine of the formula II

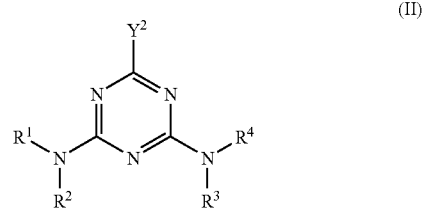

where
$Y^2$ is hydrogen, $C_1$–$C_4$-alkyl, amino or phenyl unsubstituted or substituted by $C_1$–$C_4$-alkyl, $C_1$–$C_4$-alkoxy or halogen, with the proviso that in formula II, if $Y^2$ is not amino, at least one of the radicals $R^1$ to $R^4$ is hydrogen, and
$R^1$ to $R^4$ are each as defined above, with carbonic esters in the presence of an alcohol and a base, by reacting said triazine of the formula II with dimethyl carbonate and a $C_2$–$C_{13}$-alkanol whose carbon skeleton may be interrupted by 1 or 2 oxygen atoms in ether function, in the presence of an alkali metal methoxide or alkaline earth metal methoxide as said base.

All of the alkyl radicals present in the formulae set out here may be either straight-chain or branched.

Radicals $Y^1$, $Y^2$ and X are, for example, methyl, ethyl, propyl, isopropyl, butyl, isobutyl, sec-butyl or tert-butyl.

Radicals X are further, for example pentyl, isopentyl, neopentyl, tert-pentyl, hexyl, 2-methylpentyl, heptyl, octyl, 2-ethylhexyl, isooctyl, nonyl, isononyl, decyl, isodecyl, undecyl, dodecyl, tridecyl, isotridecyl, 2-methoxyethyl, 2-ethoxyethyl, 2-propoxyethyl, 2-butoxyethyl, 2- or 3-methoxypropyl, 2- or 3-ethoxypropyl, 2- or 3-propoxypropyl, 2- or 4-methoxybutyl, 2- or 4-ethoxybutyl, 3,6-dioxaheptyl, 3,6-dioxaoctyl, 3,7-dioxaoctyl, 4,7-dioxaoctyl, 2- or 3-butoxypropyl, or 2- or 4-butoxybutyl. (The above designations isooctyl, isononyl, isodecyl, and isotridecyl are trivial names and derive from the alcohols obtained by the oxo process-cf. in this respect Ullmann's Encyclopedia of Industrial Chemistry, 5th Edition, Vol. A 1, pages 290 to 293, and Vol. A 10, pages 284 and 285.) Radicals $Y^1$ and $Y^2$ are further, for example, phenyl, 2-, 3-, or 4-methylphenyl, 2-, 3-, or 4-ethylphenyl, 2,4-dimethylphenyl, 2-, 3- or 4-methoxyphenyl, 2-, 3- or 4-ethoxyphenyl, 2,4-dimethoxyphenyl, 2-, 3- or 4-fluorophenyl, or 2-, 3- or 4-chlorophenyl.

Examples of suitable $C_2$–$C_{13}$-alkanols which may be used in the process of the invention are ethanol, propanol, isopropanol, butanol, isobutanol, sec-butanol, tert-butanol, pentanol, isopentanol, neopentanol, tert-pentanol, hexanol, 2-methylpentanol, heptanol, octanol, 2-ethylhexanol, isooctanol, nonanol, isononanol, decanol, isodecanol, undecanol, dodecanol, tridecanol, isotridecanol, 2-methoxyethanol, 2-ethoxyethanol, 2-propoxyethanol, 2-butoxyethanol, 2- or 3-methoxypropanol, 2- or 3-ethoxypropanol, 2- or 3-propoxypropanol, 2- or 4-methoxybutanol, 2- or 4-ethoxybutanol, 3,6-dioxaheptanol, 3,6-dioxaoctanol, 3,7-dioxaoctanol, 4,7-dioxaoctanol, 2- or 3-butoxypropanol, or 2- or 4-butoxybutanol.

Preference is given to using $C_2$–$C_{13}$-alkanols, the use of $C_2$–$C_7$-alkanols being mentioned in particular.

The alcohols used in the process of the invention may be employed either individually or else as mixtures with one another. In the latter case, the number of components in the mixture, and their proportions, are arbitrary.

Examples of suitable alkali metal or alkaline earth metal methoxides which may be employed in accordance with the invention include lithium, sodium, potassium, magnesium or calcium methoxide. The use of alkali metal methoxides, particularly of sodium methoxide, is preferred.

Alkali metal or alkaline earth metal methoxide may be used either in the solid aggregate state or in a dissolved or suspended form.

Preferred solvents/diluents in this case include in particular the alcohols identified above, alone or as a mixture with one another. However, it is also possible to use other conventional inert diluents.

It is also possible, furthermore, to introduce a methanolic solution of alkali metal or alkaline earth metal methoxide into the process of the invention. When this variant is practiced, the weight fraction of methanol, based on the overall weight of all alcohols used in the process (including methanol), is less than or equal to 20% by weight, preferably less than 15% by weight.

A procedure in which the reaction is performed in the presence of a catalyst is also possible.

By way of example, use may be made of phase transfer catalysts of the type as described, for example, in Ullmann's Encyclopedia of Industrial Chemistry, 5th Edition, Vol. A 19, pages 239 to 248.

Further catalysts may be metal salts or metal complexes, preferably oxides, chalcogenates, carbonates or halides of the alkali metals, alkaline earth metals or transition metals. By way of example, mention may be made here in particular of lithium chloride, magnesium chloride or sodium carbonate.

In the process of the invention, generally from 1 to 50 mol, preferably from 3 to 30 mol, of alkanol are used per mole equivalent of substitutable amino groups in the triazine of the formula II.

By substitutable amino groups in the sense of the invention are meant the following moieties: —$NH_2$ or —NH—.

Additionally, in the process of the invention, generally from 0.1 to 10 mol, preferably from 1 to 3 mol, of dimethyl carbonate are used per mole equivalent of substitutable amino groups in the triazine of the formula II.

Furthermore, in the process of the invention, generally from 0.1 to 10 mol, preferably from 1 to 3 mol equivalent, of alkali metal or alkaline earth metal methoxide are used per mole equivalent of substitutable amino groups in the triazine of the formula II.

Where the process of the invention is conducted in the presence of a catalyst, use is made generally of from $10^{-10}$ to 10% by weight, preferably from $10^{-3}$ to 1% by weight, of catalyst, based in each case on the weight of the triazine of the formula II. The process of the invention is generally conducted at a temperature from 20 to 180° C., preferably from 50 to 100° C.

It is normal to operate under atmospheric pressure but possible to use superatmospheric pressure, generally up to 8 bar.

Particular interest attaches to using triazines of the formula II in which $Y^2$ is amino as reactant in the process of the invention, and here the use of melamine (2,4,6-triamino-1,3,5-triazine) is to be very particularly stressed.

Very particular interest attaches to preparing alkoxycarbonylaminotriazines of the formula III

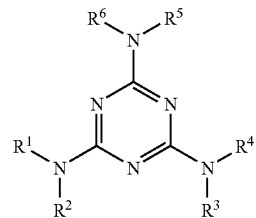

(III)

where $R^1$ to $R^6$ are each as defined above, with the proviso that three of these radicals in each case are hydrogen and the other three of these radicals are each a radical of the formula COOX, where X is as defined above, by means of the process of the invention.

Although formula I also embraces products which i) contain only a single radical COOX in the molecule in which X is methyl and/or which ii) contain two or more radicals COOX in the molecule in which X is exclusively methyl, such products alone are not to be understood as being target products of the process of the invention. At best they are obtained in a mixture with other products which a) contain only a single radical COOX in the molecule, in which X is different than methyl, and/or which b) contain two or more radicals COOX in the molecule, in which at least one radical X is different than methyl.

The process of the invention is advantageously conducted by initially introducing triazine II and alkanol and then metering in, in any order, alkali metal or alkaline earth metal methoxide, in solid state and/or in solution in alkanol, and dimethyl carbonate. It being possible for the metered addition of alkali metal or alkaline earth metal methoxide and dimethyl carbonate to take place entirely before the beginning of reaction or partly before the beginning of reaction and partly after the beginning of reaction. By removing certain amounts of alkanol from the reaction mixture by distillation before and/or during the reaction it is possible to bring about the setting of desired alkanol ratios, thereby making it possible to influence the product spectrum in a targeted way.

The alkoxycarbonylaminotriazines of the invention may be prepared in different variants (A–F).

In variant A), triazine II, alkanol, and the dissolved alkali metal or alkaline earth metal methoxide are combined. Subsequently dimethyl carbonate is added at elevated temperature, generally from 30 to 85° C.

In variant B), all of the components are introduced before the beginning of reaction.

In variant C), triazine II, alkanol, and dimethyl carbonate are introduced initially and a portion of the alkali metal or alkaline earth metal methoxide, which is partly in dissolved form and partly in the solid state, is metered in before the beginning of reaction, with the remainder being metered in after the beginning of reaction.

In variant D), triazineII, alkanol, and dimethyl carbonate are introduced initially and a portion of the alkali metal or alkaline earth metal methoxide, which is either in dissolved form or in the solid state, is metered in before the beginning of reaction, with the remainder being metered in after the beginning of reaction.

In variant E), catalysts are added before or after the beginning of reaction.

In variant F), different alkali metal methoxides (e.g. lithium methoxide and sodium methoxide) are added before or during the reaction.

The reaction regime may also be such that melamine is metered in during the reaction, in stages or in continuously.

The process of the invention can be conducted in customary reaction apparatus, e.g., a kettle reactor or tube reactor. If the new process is conducted in such a way that the molar ratio triazine of the formula II:alkanol is as high as possible, it is preferred to use apparatus having a mixing action in the case of high-viscosity or inhomogeneous reaction mixtures, e.g., kneading reactors. Also possible is the use of self-cleaning apparatus having a mixing action. Such apparatus is known per se and commercially customary. Examples of suitable such reactors are the chamber reactor, the circulation reactor or the screw reactor. The resultant reaction mixture is worked up advantageously in the absence of additional solvents.

For this purpose the alkanolic reaction mixture is contacted directly with acid, either by metering acid in or by transferring the reaction mixture into a suitable acid. The acid can be added in concentrated form with the addition of water during or after the metered addition of the acid. Particularly when using aqueous or highly concentrated acids it is necessary to ensure appropriate mixing in the course of metering. To acidify the reaction mixture it is possible to use all organic and inorganic acids which are customary and available industrially, where appropriate in a mixture with one another, in any desired concentration, but preferably in the form of aqueous solutions with a strength of from 30 to 85% by weight. It is preferred to use mineral acids whose salts are highly soluble in water, such as nitric acid, sulfuric acid or phosphoric acid or mixtures thereof, although the carboxylic acid formic acid may also be mentioned here.

Addition of acid to the reaction mixture is followed by the formation of an aqueous phase and an alkanolic phase, which are separated from one another. Phase separation is dependent on temperature and pH, and so additional water is added at a temperature of from 10 to 70° C., preferably from 15 to 50° C., and a pH of from 0 to 7, preferably from 2 to 4.

The target products result directly in the form of an alkanolic solution with a strength of from 10 to 80% by weight. Subsequent concentration of the alkanolic phase effects partial azeotropic removal of simultaneously entrained water (in the case of butanol, for example), thereby obviating further drying steps, e.g., the addition of drying agent.

The reaction mixture can be worked up following neutralization with any desired acid, of course also by extraction, washing or/and filtration.

The novel process, which may be performed either continuously or batchwise, provides the target products in high yield and purity. The alkoxycarbonylaminotriazines that are obtained by means of the process of the invention are valuable ingredients for paints.

The examples which follow are intended to illustrate the invention.

All reactions are carried out preferably in the absence of moisture. In the case of alkylcarbonylaminotriazine mixtures, the individual components were separated by HPLC (20 μl loop; UV detector (250 nm); 1 ml/min, acetonitrile: aqueous potassium dihydrogenphosphate (0.05 mol/l)=1:1; Purospher RP18e column). The quantitative indication of the components in the following examples is made in area percent (area %). Substances were identified by high resolution mass spectrometry, in some cases in the form of direct HPLC-MS coupling or by means of $^1$H and $^{13}$C NMR spectroscopy.

EXAMPLE 1

25 g (0.2 mol) of melamine, 1200 ml of butanol and 180.1 g (1 mol) of sodium methoxide (30% by weight in methanol) were charged to a vessel at a temperature of 20° C. Distillation was then carried out under reduced pressure (460 mbar) until the amount of distillate was about 130 ml. The reaction mixture was heated to about 90° C. and 59.5 g (0.66 mol) of dimethyl carbonate were added over the course of one minute. Following that addition, the inhomogeneous reaction mixture was stirred at about 95° C. for a further 90 minutes. After the mixture was cooled to about 30° C., 210 g (1 mol) of aqueous nitric acid (30% by weight) and 300 ml of water were added with stirring. The aqueous phase was separated off and the homogeneous organic phase was washed twice more with 300 ml of water each time. The organic phase is then concentrated to give a 50% strength by weight butanolic product solution containing predominantly 2,4,6-tris(butoxycarbonylamino)-1,3,5-triazine, 2-methoxycarbonylamino-4,6-bis(butoxycarbonylamino)-1,3,5-triazine, and 2,4-bis(methoxycarbonylamino)-6-butoxycarbonylamino-1,3,5-triazine (HPLC, $^1$H, $^{13}$C NMR).

EXAMPLE 2

25 g (0.2 mol) of melamine, 1872 ml of heptanol, and 180.1 g (1 mol) of sodium methoxide (30% by weight in methanol) were charged to a vessel at a temperature of 20° C. Distillation was then carried out until the amount of distillate was about 33 ml. 59.5 g (0.66 mol) of dimethyl carbonate were added to the reaction mixture at about 90° C. over the course of one minute. Following that addition, the inhomogeneous reaction mixture was stirred at 100° C. for a further 90 minutes. Direct analysis of the reaction mixture identified its principal components as 2,4,6-tris(heptyloxycarbonylamino)-1,3,5-triazine, 2-methoxycarbonylamino-4,6-bis(heptyloxycarbonylamino)-1,3,5-triazine and 2,4-bis(methoxycarbonylamino)-6-heptyloxycarbonylamino-1,3,5-triazine (HPLC, HPLC-MS).

EXAMPLE 3

Example 3 was carried out as per Example 1 but using 774 ml of ethanol instead of butanol. Direct analysis of the reaction mixture identified its principal components as 2,4,6-tris(ethoxycarbonylamino)-1,3,5-triazine, 2-methoxycarbonylamino-4,6-bis(ethoxycarbonylamino)-1,3,5-triazine, and 2,4-bis(methoxycarbonylamino)-6-ethoxycarbonylamino-1,3,5-triazine (HPLC, HPLC-MS).

EXAMPLE 4

Example 4 was carried out as per Example 1 but using 1002 ml of 2-propanol instead of butanol. Direct analysis of the reaction mixture identified its principal components as 2,4,6-tris(2-propoxycarbonylamino)-1,3,5-triazine, 2-methoxycarbonylamino-4,6-bis(2-propoxycarbonylamino)-1,3,5-triazine, and 2,4-bis(methoxycarbonylamino)-6-(2-propoxy)carbonylamino-1,3,5-triazine (HPLC, HPLC-MS).

EXAMPLE 5

Example 5 was carried out as per Example 1 but using 385 g of lithium methoxide (10% by weight in methanol) instead of sodium methoxide. Direct analysis of the reaction mixture identified its principal components as 2,4,6-tris(butoxycarbonylamino)-1,3,5-triazine, 2-methoxycarbonylamino-4,6-bis(butoxycarbonylamino)-1,3,5-triazine, and 2,4-bis(methoxycarbonylamino)-6-butoxycarbonylamino-1,3,5-triazine (HPLC, HPLC-MS).

EXAMPLE 6

25 g (0.2 mol) of melamine, 300 ml of butanol, 115.8 g (0.64 mol) of sodium methoxide (30% by weight in methanol), 19.3 g (0.36 mol) of sodium methoxide and 59.5 g (0.66 mol) of dimethyl carbonate were charged to a vessel at 20° C. The reaction mixture was heated to 95° C. and stirred at this temperature for about 60 minutes. The reaction mixture was worked up as set out in Example 1, and contained predominantly 2,4,6-tris(butoxycarbonylamino)-1,3,5-triazine, 2-methoxycarbonylamino-4,6-bis(butoxycarbonylamino)-1,3,5-triazine, and 2,4-bis(methoxycarbonylamino)-6-butoxycarbonylamino-1,3,5-triazine (HPLC).

EXAMPLE 7

Example 7 was carried out as per Example 6 but at a pressure of about 2 bar and a reaction temperature of 80° C. The reaction mixture was worked up as set out in Example 1 and contained predominantly 2,4,6-tris(butoxycarbonylamino)-1,3,5-triazine, 2-methoxycarbonylamino-4,6-bis(butoxycarbonylamino)-1,3,5-triazine, and 2,4-bis(methoxycarbonylamino)-6-butoxycarbonylamino-1,3,5-triazine (HPLC).

EXAMPLE 8

50 g (0.4 mol) of melamine, 134 ml of butanol, 151.3 g (2.8 mol) of sodium methoxide (solid) and 144 g (1.6 mol) of dimethyl carbonate were introduced into a kneading reactor (List reactor) at a temperature of 20° C. Subsequently the reaction mixture was kneaded at 75° C. for 1 hour. Direct analysis of the reaction mixture identified its main components as 2,4,6-tris(methoxycarbonyl-amino-1,3,5-triazine, 2-butoxycarbonylamino-4,6-bis(methoxy-carbonylamino)-1,3,5-triazine and 2,4-bis(butoxycarbonyl-amino)-6-methoxycarbonylamino-1,3,5-triazine, 2,4,6-tris(butoxy-carbonylamino)-1,3,5-triazine (HPLC, HPLC-MS).

EXAMPLE 9

25.2 g (0.2 mol) of melamine, 1200 ml of butanol, 75.6 g (1.4 mol) of sodium methoxide (solid) and 72.06 g (0.8 mol) of dimethyl carbonate were introduced into a reaction vessel at a temperature of 20° C. The reaction mixture was subsequently heated to about 70° C. and stirred at about 70° C. for a further 90 minutes. After the mixture had been cooled to about 30° C. 294 g (1.4 mol) of aqueous nitric acid (30% strength by weight) and 300 ml of water were added with stirring. The aqueous phase was separated off and the organic homogeneous phase was washed a further 2 times with 300 ml of water each time. Concentration of the organic phase gave a 50% strength by weight butanolic product solution which contained predominantly 2,4,6-tris(butoxycarbonylamino)-1,3,5-triazine, 2-methoxycarbonylamino-4,6-bis(butoxycarbonyl-amino)-1,3,5-triazine and 2,4-bis(methoxycarbonylamino)-6-butoxycarbonylamino-1,3,5-triazine (HPLC, $^1$H-, $^{13}$C NMR).

EXAMPLE 10

The reaction was conducted in as per example 9 but instead of nitric acid, after the mixture had been cooled to about 30° C. 97 g (1 mol) of aqueous phosphoric acid (85% strength by weight) and 600 ml of water were added with stirring. The aqueous phase was separated off and the organic homogeneous phase was washed a further 2 times with 300 ml of water each time. Concentration of the organic phase gave a 50% strength by weight butanolic product solution which contained predominantly 2,4,6-tris(butoxycarbonyl-amino)-1,3,5-triazine, 2-methoxycarbonylamino-4,6-bis(butoxy-carbonylamino)-1,3,5-triazine and 2,4-bis(methoxycarbonyl-amino)-6-butoxycarbonylamino-1,3,5-triazine (HPLC, $^1$H-, $^{13}$C NMR).

EXAMPLE 11

The reaction was conducted as per examples 9 and 10, but during the washing operation the pH of the mixture was kept below 3 by adding nitric acid. Further workup as per example 10 gave a 50% strength by weight butanolic product solution which contained predominantly 2,4,6-tris(butoxycarbonyl-amino)-1,3,5-triazine, 2-methoxycarbonylamino-4,6-bis(butoxy-carbonylamino)-1,3,5-triazine and 2,4-bis(methoxycarbonyl-amino)-6-butoxycarbonylamino-1,3,5-triazine (HPLC, $^1$H-, $^{13}$C NMR).

EXAMPLE 12

The reaction was conducted as per example 9 but instead of nitric acid, after the mixture had been cooled to about 30° C. 458 g (0.7 mol) of aqueous sulfuric acid (50% strength by weight) and 600 ml of water were added with stirring. The aqueous phase was separated off and the organic homogeneous phase was washed a further 2 times with 300 ml of water each time. Concentration of the organic phase gave a 50% strength by weight butanolic product solution which contained predominantly 2,4,6-tris(butoxycarbonyl-amino)-1,3,5-triazine, 2-methoxycarbonylamino-4,6-bis(butoxy-carbonylamino)-1,3,5-triazine and 2,4-bis(methoxycarbonyl-amino)-6-butoxycarbonylamino-1,3,5-triazine (HPLC, $^1$H-, $^{13}$C NMR).

EXAMPLE 13

29 g (0.23 mol) of melamine, 82.9 g (0.92 mol) of dimethyl carbonate and 87 g (1.61 mol) of sodium methoxide were placed in 1200 ml of butanol. The reaction mixture was stirred at 78° C. for 3 hours. After the mixture had cooled to room temperature, 338.2 g (286.6 ml) of 30% strength by weight aqueous nitric acid were metered in over the course of 1 minute. After the aqueous phase had been separated off, the mixture was washed 3 times with 200 ml of water each time. Distillative removal of water and butanol gave a 50% strength by weight butanolic solution containing as its main components 2,4,6-tris(butoxycarbonyl-amino)-1,3,5-triazine, 2-methoxycarbonylamino-4,6-bis-(butoxycarbonylamino)-1,3,5-triazine and 2,4-bis(methoxycarbonyl-amino)-6-butoxycarbonylamino-1,3,5-triazine (HPLC, $^1$H-, $^{13}$C-NMR).

EXAMPLE 14

The reaction was conducted as per example 13 except that the melamine was metered in 4 equal portions over the course of 1.5 hours into the initial charge of dimethyl carbonate, sodium methoxide and butanol. Working up was likewise as described in example 13. This gave a 50% strength by weight butanolic solution containing as its main components 2,4,6-tris(butoxycarbonyl-amino)-1,3,5-triazine, 2-methoxycarbonylamino-4,6-bis-(butoxy-carbonylamino)-1,3,5-triazine and 2,4-bis(methoxycarbonyl-amino)-6-butoxycarbonylamino-1,3,5-triazine (HPLC, $^1$H-, $^{13}$C-NMR).

EXAMPLE 15

2.9 kg (23 mol) of melamine, 120 l of butanol, 8.7 kg (161 mol) of sodium methoxide and 8.3 kg (92 mol) of dimethyl carbonate were combined and heated to 85° C. over the course of 1 hour with stirring. The reaction mixture was stirred at 85° C. for 2.5 hours more and then cooled to 35° C. With vigorous stirring 33.8 kg (161 mol) of 30% strength by weight aqueous nitric acid were added and, after a further 15 minutes, stirring was ended. Following phase separation, the aqueous phase was separated off and discarded. The organic phase was washed 3 times with 20 l of water each time. Subsequently the organic phase was concentrated under reduced pressure. The resultant solution, with a strength of approximately 50% by weight, contained predominantly 2,4,6-tris(butoxycarbonylamino)-1,3,5-triazine (19.5 area %), 2-methoxycarbonylamino-4,6-bis(butoxycarbonylamino)-1,3,5-triazine (41.5 area %), 2,4-bis(butoxycarbonylamino)-6-amino-1,3,5-triazine (2.8 area %), 2,4-bis(methoxycarbonylamino)-6-butoxycarbonylamino-1,3,5-triazine (25.6 area %), 2-methoxy-carbonylamino-4-butoxycarbonylamino-6-amino-1,3,5-triazine (3.4 area %) and tris(methoxycarbonylamino)-1,3,5-triazine (4.6 area %).

EXAMPLE 16

The reaction was conducted as per example 15 except that the mixture was heated to 80° C. over the course of an hour. Subsequently about 15 l of solvent were distilled off over the course of 30 minutes under reduced pressure. The reaction mixture was stirred at 80° C. for 2.5 hours more and then cooled to 35° C. Workup takes place as described in example 15. The resultant solution, with a strength of approximately 50% by weight, contained predominantly 2,4,6-tris(butoxycarbonylamino)-1,3,5-triazine (25.9 area %), 2-methoxycarbonylamino-4,6-bis(butoxy-carbonylamino)-1,3,5-triazine (44.6 area %), 2,4-bis(butoxycarbonylamino)-6-amino-1,3,5-triazine (2.4 area %), 2,4-bis(methoxycarbonylamino)-6-butoxycarbonylamino-1,3,5-triazine (21.0 area %), 2-methoxycarbonylamino-4-butoxycarbonylamino-6-amino-1,3,5-triazine (3.3 area %) and tris(methoxycarbonylamino)-1,3,5-triazine (2.0 area %).

EXAMPLE 17

The reaction was conducted as per example 16 except that following distillative removal of 15 l of solvent stirring at 80° C. was carried out for only 2 hours, after which about 15 l of solvent were distilled off again over 30 minutes, before the reaction mixture was cooled to 35° C. Workup took place as described in example 15. The resultant solution, with a strength of approximately 50% by weight, contained predominantly 2,4,6-tris(butoxycarbonylamino)-1,3,5-triazine (28.1 area %), 2-methoxycarbonylamino-4,6-bis(butoxycarbonylamino)-1,3,5-triazine (42.75 area %), 2,4-bis(butoxycarbonylamino)-6-amino-1,3,5-triazine (3.0 area %), 2,4-bis(methoxycarbonylamino)-6-butoxycarbonylamino-1,3,5-triazine (18.4 area %), 2-methoxycarbonylamino-4-butoxycarbonylamino-6-amino-1,3,5-triazine (4.8 area %) and tris(methoxycarbonylamino)-1,3,5-triazine (1.8 area %).

EXAMPLE 18

120 l of butanol and 8.7 kg (161 ml) of sodium methoxide were heated at 85° C. under reduced pressure, with solvent being removed by distillation in the course of heating. Subsequently the resultant mixture was admixed with 2.9 kg (23 mol) of melamine and 8.3 kg (92 mol) of dimethyl carbonate, with stirring. After 2 hours of stirring at 85° C. the reaction mixture was cooled and admixed with 39.45 kg (80.5 mol) of 20% strength by weight aqueous sulfuric acid, with vigorous stirring. Further workup took place as described in example 15. The resultant solution, with a strength of approximately 50% by weight, contained the same main components as in example 15 (HPLC-MS). The tris-(butoxycarbonylamino)-1,3,5-triazine content was 36 area % (HPLC).

EXAMPLE 19

The reaction was conducted as per example 18 but with continuous removal of a solvent stream (distillation) during the reaction at 85° C. The reaction mixture was worked up as described in example 15. The 50% strength by weight product solution contained predominantly tris(butoxycarbonylamino)-1,3,5-triazine, whose proportion was 69 area % (HPLC).

EXAMPLE 20

The reaction was carried out as per example 19, but during the reaction the solvent removed by distillation was partially replaced by butanol. Workup took place as per example 15. Complete concentration of the reaction mixture gave a solid consisting predominantly of tris(butoxycarbonylamino)-1,3,5-triazine (98 area %) (HPLC). The product was recrystallized from acetonitrile/n-hexane (diffusion).

Analysis: calc.: C 50.69, H 7.1, O 22.5, N 19.71; found: C 49.5, H 7.3, O 23.1, N 18.6.

We claim:

1. A process for preparing one or more alkoxycarbonylaminotriazines of formula III

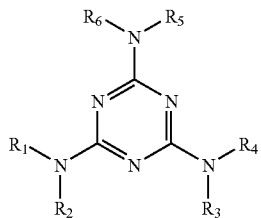

wherein $R^1$, $R^2$, $R^3$, $R^4$, $R^5$ and $R^6$ independently of one another are each hydrogen or a radical of the formula COOX or X, wherein X is $C_1$–$C_{13}$-alkyl, whose carbon skeleton may be interrupted by 1 or 2 oxygen atoms in ether function, with the proviso that three of these radicals, in each case, are hydrogen and the three remaining radicals are each a radical of the formula COOX, comprising reacting a triazine of the formula II

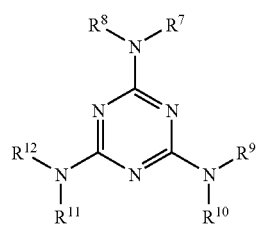

wherein $R^7$ to $R^{12}$, independently of one another, are each hydrogen or a radical of the formula COOX or X, wherein X is a $C_1$–$C_{13}$-alkyl, whose carbon skeleton may be interrupted by 1 or 2 oxygen atoms in ether function, with a carbonic ester in the presence of an alcohol and a base, which comprises reacting said triazine of the formula II with dimethyl carbonate and a $C_2$–$C_{13}$-alkanol whose carbon skeleton may be interrupted by 1 or 2 oxygen atoms in ether function, in the presence of an alkali metal methoxide or alkaline earth metal methoxide as said base to form the one or more alkoxycarbonylaminotriazines of the formula III.

2. The process as claimed in claim 1, wherein a $C_2$–$C_{13}$-alkanol is used.

3. The process as claimed in claim 1, wherein an alkali metal methoxide is used as said base.

4. The process as claimed in claim 1, wherein the reaction is conducted at a temperature from 20 to 180° C.

5. The process as claimed in claim 1, wherein the reaction is performed with from 1 to 50 mol of alkanol, based in each case on one mole equivalent of substitutable amino groups in said triazine of the formula II.

6. The process as claimed in claim 1, wherein the reaction is performed with from 0.1 to 10 mol of dimethyl carbonate, based in each case on one mole equivalent of substitutable amino groups in said triazine of the formula II.

7. The process as claimed in claim 1, wherein the reaction is performed with from 0.1 to 10 mol equivalent of alkali metal methoxide or alkaline earth metal methoxide, based in each case on one mole equivalent of substitutable amino groups in said triazine of the formula II.

8. The process as claimed in claim 1, wherein triazine II and alkanol are introduced initially and then in any order alkali metal or alkaline earth metal methoxide, in solid sate and/or in solution in alkanol, and dimethyl carbonate are metered in, it being possible for the metering of alkali metal or alkaline earth metal methoxide and dimethyl carbonate to take place completely before the beginning of reaction or partly before the beginning of reaction and partly after the beginning of reaction.

* * * * *